(12) United States Patent
Yasunaga et al.

(10) Patent No.: US 10,244,925 B2
(45) Date of Patent: Apr. 2, 2019

(54) ENDOSCOPE (71) Applicant: OLYMPUS CORPORATION, Tokyo (JP)

(72) Inventors: Koji Yasunaga, Hino (JP); Mitsutaka Kokubo, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/623,931

(22) Filed: Jun. 15, 2017

(65) Prior Publication Data
US 2017/0280980 A1 Oct. 5, 2017

Related U.S. Application Data (63) Continuation of application No. PCT/JP2016/067018, filed on Jun. 8, 2016.

(30) Foreign Application Priority Data

Jul. 14, 2015 (JP) ................................. 2015-140685

(51) Int. Cl.
*A61B 1/00* (2006.01)
*G02B 23/24* (2006.01)
(Continued)

(52) U.S. Cl.
CPC ...... *A61B 1/00183* (2013.01); *A61B 1/00096* (2013.01); *A61B 1/00172* (2013.01);
(Continued)

(58) Field of Classification Search
CPC ............ A61B 1/00066; A61B 1/00172; A61B 1/00183; A61B 1/00096; G02B 23/2446
See application file for complete search history.

(56) References Cited

U.S. PATENT DOCUMENTS 5,689,365 A    11/1997   Takahashi
6,371,909 B1 *   4/2002   Hoeg ................. A61B 1/00183
                                                                                   600/112
(Continued)

FOREIGN PATENT DOCUMENTS

EP       0 050 922 A2    5/1982
EP       1683472 A1     7/2006
(Continued)

OTHER PUBLICATIONS

Extended Supplementary European Search Report dated Jun. 26, 2018 in European Patent Application No. 16 82 4178.4.
(Continued)

*Primary Examiner* — Aaron B Fairchild
(74) *Attorney, Agent, or Firm* — Scully, Scott, Murphy & Presser, P.C.

(57) ABSTRACT

An endoscope includes: an image pickup portion including an image pickup device; an optical axis bending optical system; an operation input portion which pivots; an operation conversion portion that resolves an input of the operation input portion and generate a plurality of outputs; and an operation transmission portion that transmits the outputs of the operation conversion portion to a plurality of movable portions. The optical axis bending optical system includes a first prism rotatably supported around a second optical axis, and a second prism rotatably supported around a third optical axis. The operation transmission portion includes: an image pickup portion interlocking portion rotatably supporting the image pickup portion; and a prism rotation transmission portion including a first transmission member that rotates the first prism around the second optical axis, and a second transmission member that rotates the second prism around the third optical axis integrally with the first prism.

9 Claims, 7 Drawing Sheets (51) Int. Cl.
*G02B 23/02* (2006.01)
*H04N 5/225* (2006.01)
*A61B 1/05* (2006.01)

(52) U.S. Cl.
CPC .............. *A61B 1/051* (2013.01); *G02B 23/02* (2013.01); *G02B 23/24* (2013.01); *G02B 23/2423* (2013.01); *G02B 23/2446* (2013.01); *H04N 5/2256* (2013.01); *A61B 1/00066* (2013.01)

(56) References Cited

U.S. PATENT DOCUMENTS

| | | |
|---|---|---|
| 2005/0177026 A1 | 8/2005 | Hoeg et al. |
| 2006/0206006 A1 | 9/2006 | Schara et al. |
| 2006/0252995 A1 | 11/2006 | Hoeg et al. |
| 2011/0199471 A1 | 8/2011 | Tomioka |
| 2013/0044361 A1 | 2/2013 | Katakura |
| 2016/0331212 A1* | 11/2016 | Yasunaga ........... A61B 1/00183 |

FOREIGN PATENT DOCUMENTS

| | | |
|---|---|---|
| EP | 1690492 A1 | 8/2006 |
| EP | 2369395 A1 | 9/2011 |
| EP | 2624039 A1 | 8/2013 |
| JP | H08-82766 A | 3/1996 |
| JP | 2006-201796 A | 8/2006 |
| JP | 2006-223866 A | 8/2006 |
| JP | 4746723 B2 | 8/2011 |
| JP | 5372261 B2 | 12/2013 |
| WO | 99/42028 A1 | 8/1999 |
| WO | WO 2011/013518 A1 | 2/2011 |
| WO | WO 2012/081349 A1 | 6/2012 |

OTHER PUBLICATIONS

International Search Report dated Sep. 6, 2016 issued in PCT/JP2016/067018.

* cited by examiner

ENDOSCOPE

CROSS REFERENCE TO RELATED APPLICATION

This application is a continuation application of PCT/JP2016/067018 filed on Jun. 8, 2016 and claims benefit of Japanese Application No. 2015-140685 filed in Japan on Jul. 14, 2015, the entire contents of which are incorporated herein by this reference.

BACKGROUND OF INVENTION

1. Field of the Invention

The present invention relates to an endoscope of a type in which an observation field of view direction is variable and which is configured to be capable of changing the observation field of view direction by moving optical elements provided in a distal end portion of an insertion portion.

2. Description of the Related Art

Conventionally, endoscopes that are configured to include an elongated tube-shaped insertion portion are widely used in, for example, a medical field and an industrial field. Among such endoscopes, medical endoscopes used in the medical field are configured so that, by inserting an insertion portion into a subject, for example, into a body cavity of a living organism to acquire an optical image, an organ or the like can be observed and, as necessary, various kinds of treatment can be performed on the organ or the like using a treatment instrument that is inserted into a treatment instrument insertion channel provided in the endoscope. Further, industrial endoscopes that are used in the industrial field are configured so that, by inserting an insertion portion into an object, for example, into an apparatus such as a jet engine or piping in a plant or into a structure such as a facility to acquire an optical image, the state inside the relevant object can be observed or inspected, for example, observation or inspection of the state of flaws or corrosion can be performed.

Conventional medical endoscopes include endoscopes that have a flexible insertion portion and which are used for examining and treating a digestive tract, and also include endoscopes that have a rigid insertion portion which are used for surgery. In particular, endoscopes that have a rigid insertion portion are called "rigid endoscopes", "laparoscopes", "nephroscopes" or the like.

Among such conventional endoscopes, various endoscopes have been disclosed such as in International Publication No. 2012-081349, that are equipped with a so-called "rotating prism mechanism" that is configured to be capable of changing an incident direction (direction in which an optical axis is directed) of an incident light beam by moving an incident surface of a prism that is an optical element provided at a distal end of an endoscope insertion portion by causing the prism to rotate, and can thus freely change an observation field of view direction (oblique viewing angle).

An endoscope disclosed in the aforementioned International Publication No. 2012-081349 and the like includes: a first prism that deflects light that entered along an incident light axis to thereby emit the light in a direction along a first axis line that is substantially orthogonal to the incident light axis; and a second prism that has a first reflecting surface which deflects the light that is emitted from the first prism, in a second axis line direction that is substantially orthogonal to the first axis line and that is disposed facing the first prism; and the endoscope is configured so that the first prism is rotatable relative to the second prism around the first axis line.

SUMMARY OF THE INVENTION

An endoscope according to one aspect of the present invention includes: an image pickup portion including an image pickup device; an optical axis bending optical system including a plurality of prisms for guiding a light beam from an object to a light receiving surface of the image pickup portion; operation input means which can be pivoted; operation conversion means configured to resolve an input from the operation input means and generate a plurality of outputs; and a plurality of operation transmission means configured to transmit the plurality of outputs that are outputted from the operation conversion means to a respectively corresponding plurality of movable portions; wherein the operation transmission means includes image pickup portion interlocking means that rotatably supports the image pickup portion around a longitudinal axis, and prism rotation transmission means configured to rotate the plurality of prisms of the optical axis bending optical system.

DETAILED DESCRIPTION OF THE PREFERRED EMBODIMENT(S)

Hereunder, the present invention is described by way of embodiments that illustrated in the accompanying drawings. The respective drawings used for the following description are drawings that schematically illustrate the present invention, and the dimensional relation between the respective members and the contraction scale and the like are varied for each component so as to show the respective components in a size that is recognizable in the drawings. Accordingly, the present invention is not limited to only the quantity of components, the shapes of components, the ratios between the sizes of components, and the relative positional relationship between the respective components illustrated in each of the accompanying drawings.

First Embodiment

Figure 1:
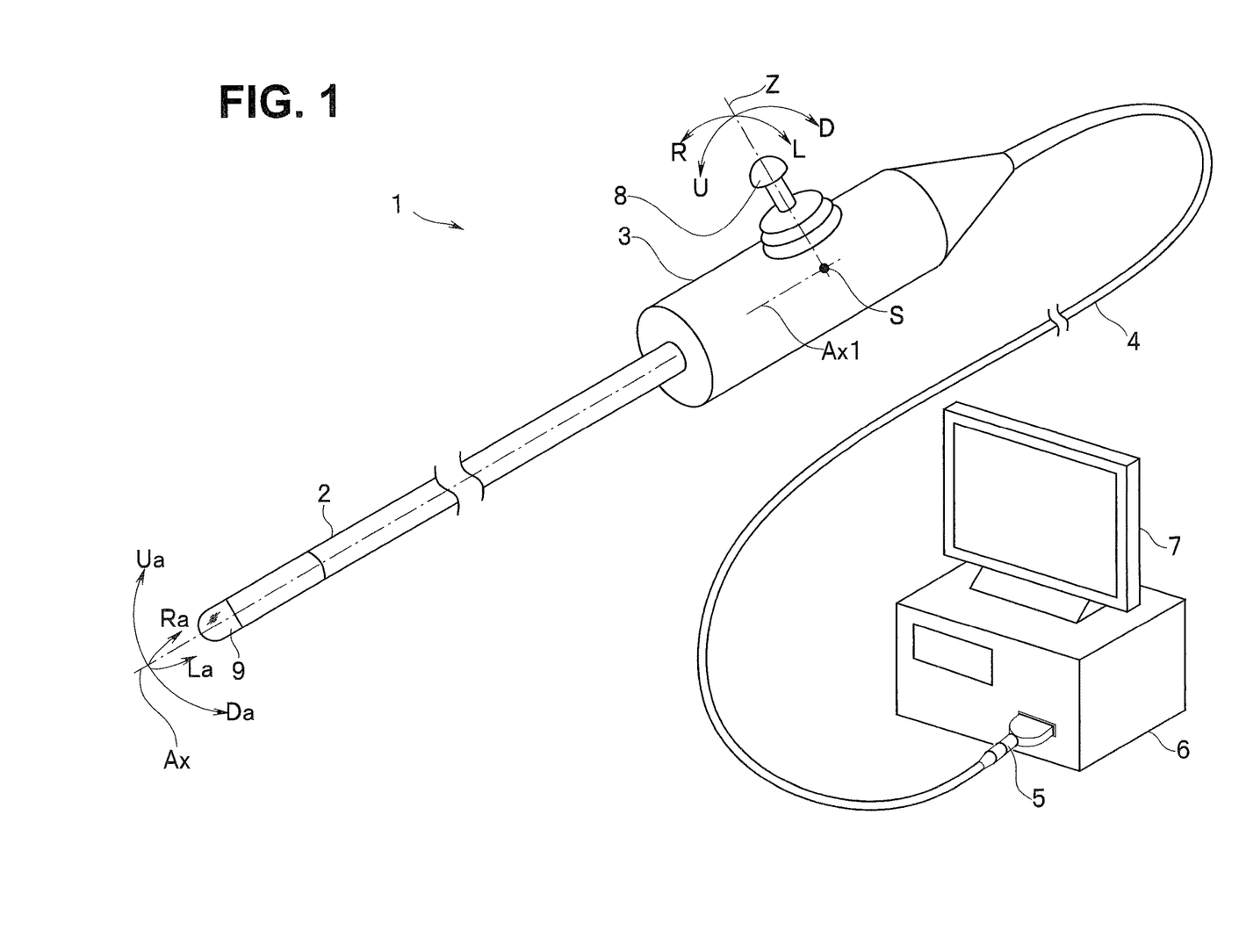
FIG. 1 is a schematic perspective view illustrating the overall configuration of an endoscope system including an endoscope according to a first embodiment of the present invention.
Figure 2:
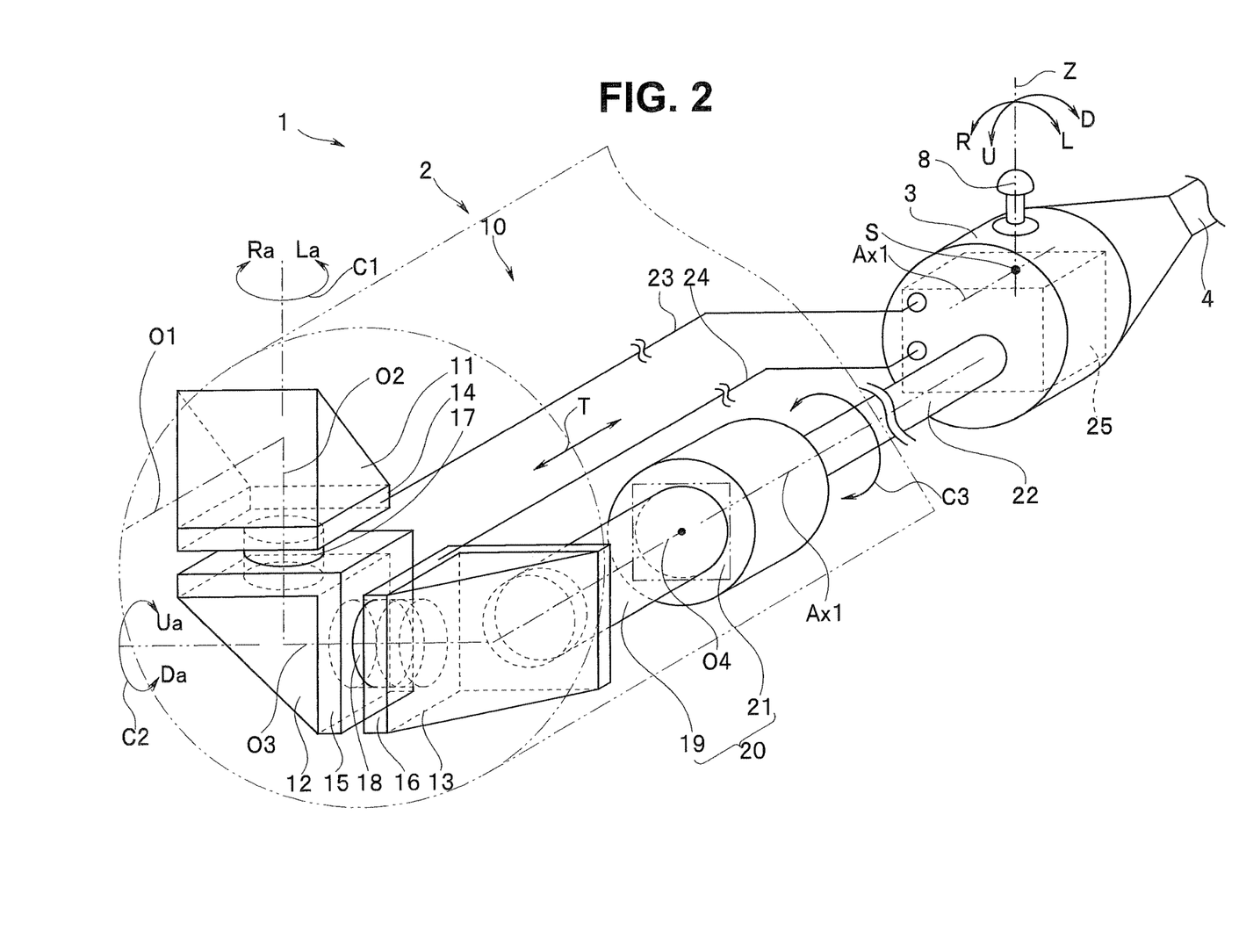
FIG. 2 is a conceptual diagram illustrating an example of the configuration of a field of view switching mechanism in the endoscope according to the first embodiment of the present invention.
Figure 3:
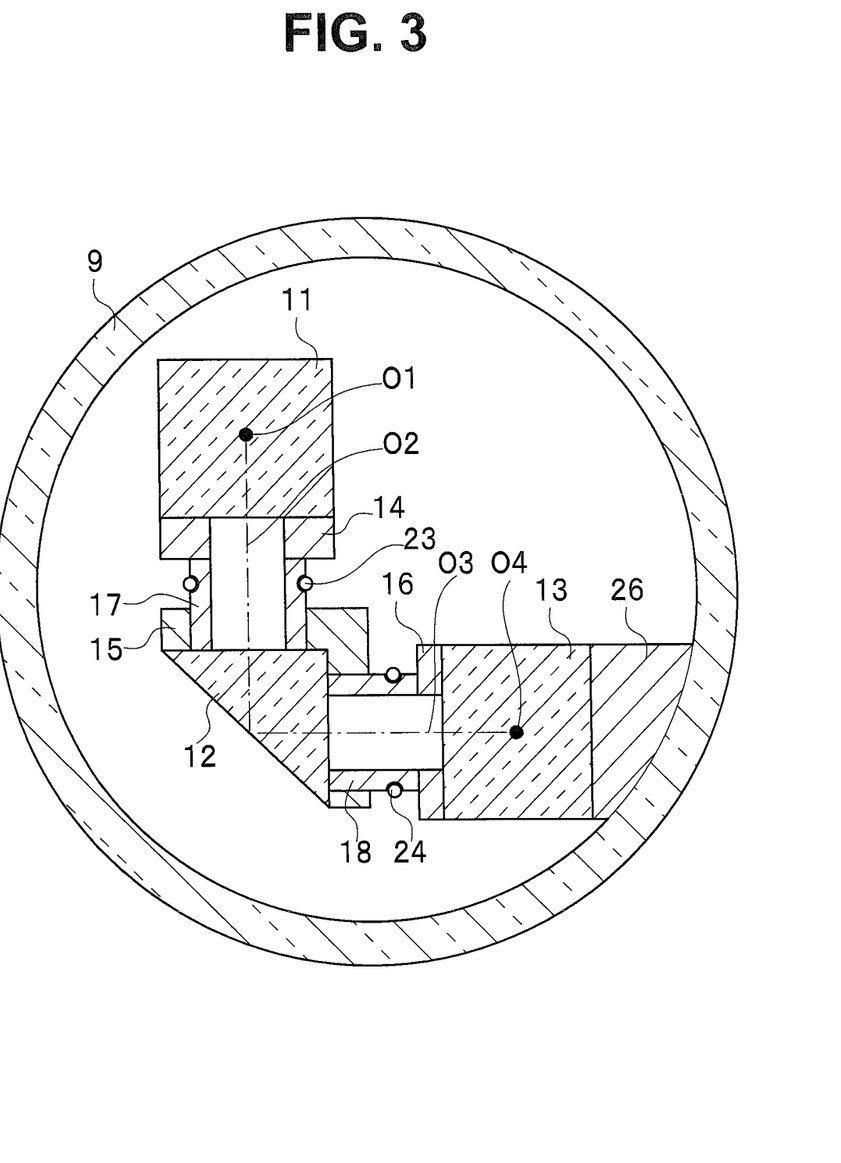
FIG. 3 is a cross-sectional view of a distal end portion in the endoscope according to the first embodiment of the present invention.
Figure 4:
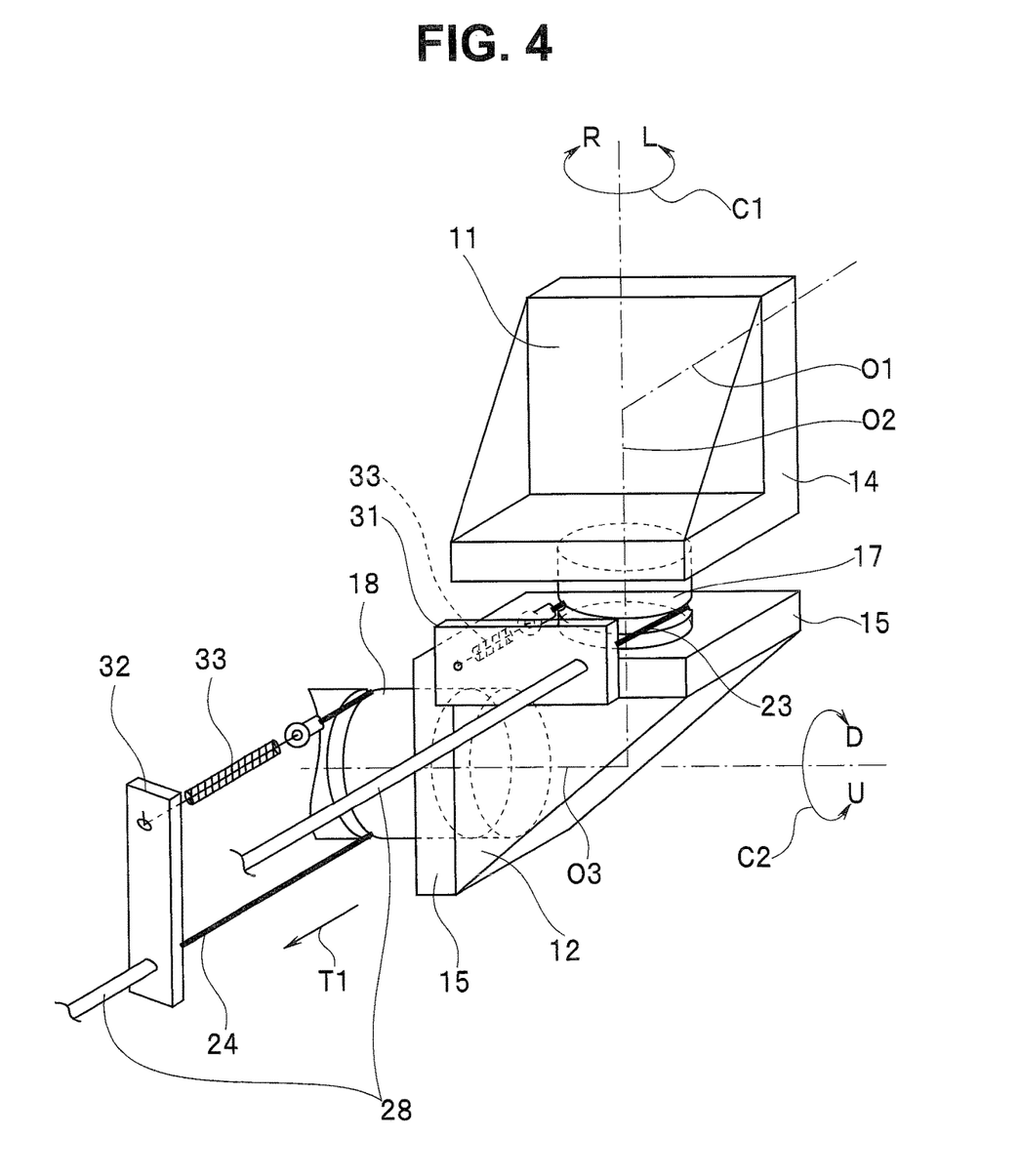
FIG. 4 is a conceptual diagram illustrating an example of the configuration of a prism rotation mechanism of operation transmission means of the field of view switching mechanism in the endoscope according to the first embodiment of the present invention.
Figure 5:
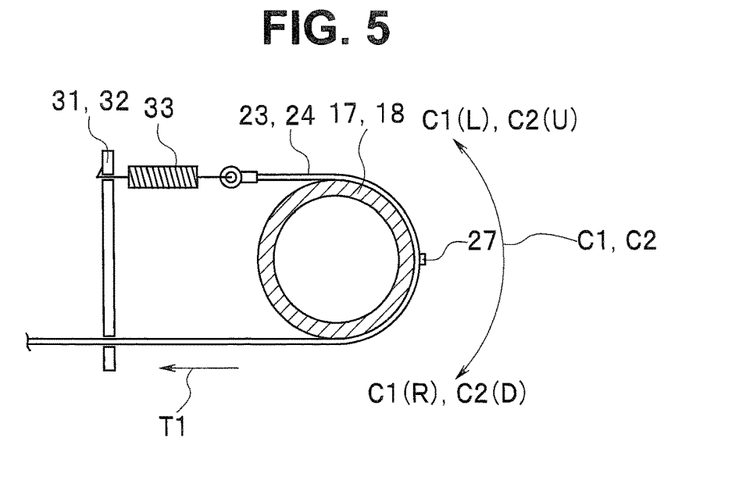
FIG. 5 is a configuration diagram illustrating an example of a form of fixedly disposing a pulling wire in the prism rotation mechanism illustrated in FIG. 4.
Figure 6:
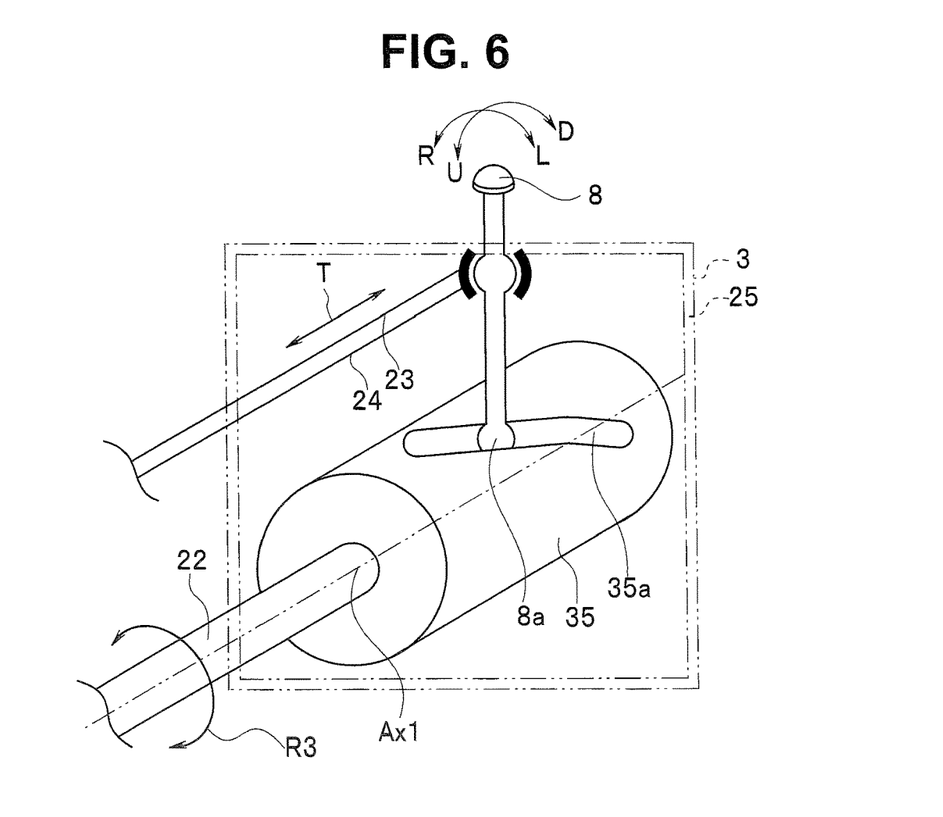
FIG. 6 is a conceptual diagram illustrating an example of an interlocking configuration with respect to image pickup portion interlocking means of operation conversion means of the field of view switching mechanism in the endoscope according to the first embodiment of the present invention.
Figure 7:
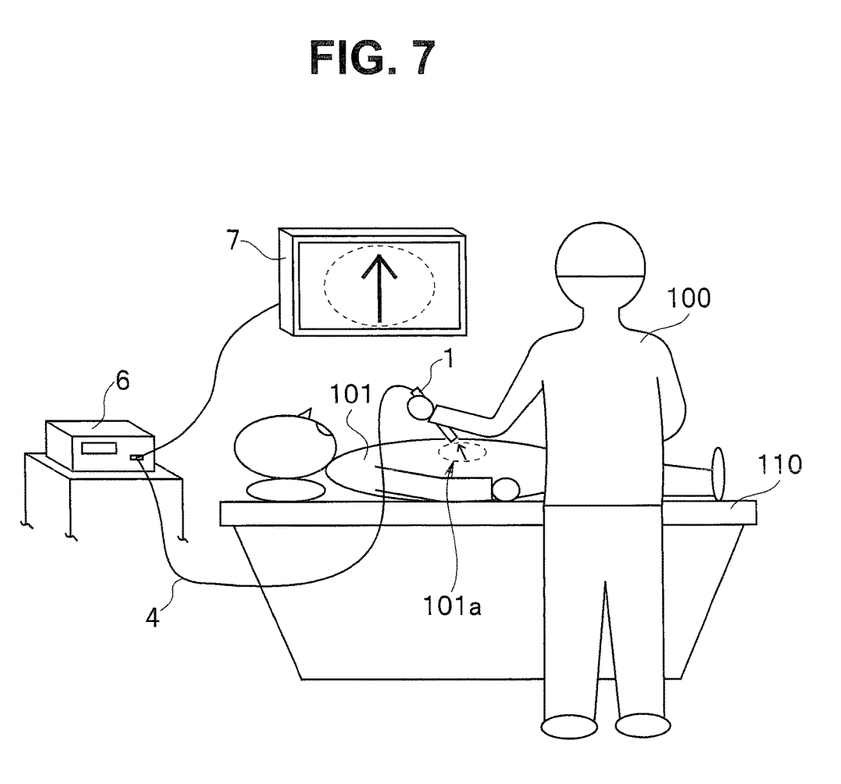
FIG. 7 is an explanatory drawing for describing operation of the endoscope according to the first embodiment of the present invention, which is a drawing that illustrates a usage environment of the endoscope.

FIG. 1 to FIG. 7 are views that illustrate a first embodiment of the present invention. FIG. 1 is a schematic perspective view illustrating an overall configuration of an endoscope system including an endoscope of the present embodiment. FIG. 2 is a view that conceptually illustrates an example of a configuration of a field of view switching mechanism in the endoscope of the present embodiment. FIG. 3 is a cross-sectional diagram of a distal end portion in the endoscope of the present embodiment. Note that FIG. 3 illustrates a transverse section that is orthogonal to an insertion axis Ax of an insertion portion 2. By the means FIG. 3 illustrates the arrangement of a plurality of prisms in the field of view switching mechanism shown in FIG. 2. FIG. 4 is a view that conceptually illustrates an example of a configuration of a prism rotation mechanism in operation transmission means of the field of view switching mechanism in the endoscope of the present embodiment. FIG. 5 is a configuration diagram illustrating an example of a form of fixedly disposing a pulling wire in the prism rotation mechanism illustrated in FIG. 4. FIG. 6 is a view that conceptually illustrates an example of an interlocking configuration with respect to image pickup portion interlocking means of operation conversion means of the field of view switching mechanism in the endoscope according to the present embodiment. FIG. 7 is an explanatory drawing for describing operation of the endoscope according to the present embodiment, which is a drawing that illustrates a usage environment of the endoscope.

[Overall Configuration of Endoscope System]

First, before describing the details of the endoscope of the present embodiment, the overall configuration of an endoscope system that includes the present endoscope will be briefly described using FIG. 1.

The endoscope of the present embodiment is, for example, a medical instrument that is configured in a form that can be introduced into a subject such as a human body and that is specifically used for surgery or examining urinary organs or the like, and has a configuration that optically picks up images of a predetermined observation site inside the subject. A subject into which the present endoscope 1 is introduced is not limited to the aforementioned human body or the like, and may be another living organism or may also be an artifact such as a machine or building.

The endoscope of the present embodiment may be of a form, insertion portion of which does not have flexibility, and forms referred to as a so-called "rigid endoscope", "laparoscope" or "nephroscope" may be mentioned as examples of such an endoscope.

As illustrated in FIG. 1, an endoscope system including such an endoscope is constituted by the endoscope 1, an external apparatus 6 to which the endoscope 1 is connected, and a display apparatus 7 that is connected to the external apparatus 6 and the like.

The endoscope 1 is mainly constituted by a rigid insertion portion 2 that is introduced into a subject, an operation portion 3 that is located at a proximal end of the insertion portion 2, and a universal cord 4 that is extended from the proximal end portion of the operation portion 3.

A connector portion 5 that secures a connection with the external apparatus 6 is connected to a proximal end portion of the universal cord 4.

The external apparatus 6, for example, includes a so-called "video processor" constituted by an electrical circuit that configures an image processing portion or the like, and a light source apparatus (not illustrated in the drawings) that supplies an illuminating light to the distal end portion of the endoscope 1. The aforementioned image processing portion has a function for receiving an image pickup signal or the like that is outputted from an image pickup portion 20 (to be described later) of the endoscope 1, and generating a video signal based on the received image pickup signal and outputting the video signal to the display apparatus 7. Thus, the endoscope system of the present embodiment is configured to be capable of displaying an optical image (endoscopic image) picked up by the image pickup portion as a video using the display apparatus 7.

In the endoscope 1, the insertion portion 2 is mainly constituted by a pipe member having a straight tube shape that is formed by a rigid member. The proximal end side of the insertion portion 2 is connected to the distal end side of the operation portion 3. A distal end cover 9 that serves as an observation window that is formed by a transparent member, distal end of which is formed in a hemispherical shape, is provided in the distal end portion of the insertion portion 2. Note that an insertion axis of the insertion portion 2 is denoted by reference characters Ax.

In addition to constituent members such as the image pickup portion 20 (see FIG. 2) and an illumination unit (not illustrated in the drawings), some constituent members (to be described in detail later; see FIG. 2 to FIG. 6) of a field of view switching mechanism 10 and the like are also housed inside the distal end portion of the insertion portion 2. The constituent members are substantially the same as constituent members provided in a common endoscope.

Further, in addition to a signal wire (not illustrated in the drawings), an illumination cable (not illustrated in the drawings) and the like that are extended from the image pickup portion 20, a rotating shaft 22 (image pickup portion interlocking means that is one portion of the field of view switching mechanism 10; see FIG. 2 and the like) for making a part of the image pickup portion 20 freely rotatable around an axis Ax1 that is substantially parallel to the insertion axis Ax of the insertion portion 2 is also inserted through and disposed inside the insertion portion 2. The signal wire, illumination cable and rotating shaft 22 reach as far as the inside of the operation portion 3. In addition, the signal wire and illumination cable and the like are inserted through the inside of the universal cord 4 and reach as far as the connector portion 5.

Further, in the endoscope 1, the operation portion 3 is configured to include a plurality of operation members for operating the endoscope 1. As a principal operation member among the plurality of operation members, an operation lever 8 is provided that is a so-called "joystick-type" operation member of a form that, for example, operates a rod-like member that is configured to be pivoted, by tilting the rod-like member around a predetermined rotation center axis. The operation lever 8, for example, is an operation member that is used for switching a field of view of an endoscopic image. Note that illustration of operation members other than the operation lever 8 is omitted from FIG. 1.

The operation lever 8 is arranged so as to protrude in one direction from the side face of the operation portion 3. In this case, in a normal neutral state, the operation lever 8 is erectly provided so as to maintain a direction (denoted by reference character Z in FIG. 1) that is substantially orthogonal to the insertion axis Ax. The operation lever 8 is pivotally supported steplessly and rotatably for 360 degrees around the protruding direction axis Z in a manner that takes an intersecting point S between the protruding direction axis Z and the axis Ax1 that is substantially parallel to the insertion axis Ax as a support point. Note that the operation lever 8 is configured so that the neutral state is always maintained by unshown urging means. The configuration is a well-known configuration for common joystick-type operation members. Therefore, illustration of a detailed configuration for maintaining the operation lever 8 in the neutral state is omitted from the drawings.

Note that operation conversion means 25 configured to resolve a tilting operation of the operation lever 8 among some of the constituent members of the field of view switching mechanism 10 and output a corresponding output is arranged inside the operation portion 3. The operation lever 8 is interlocked with the operation conversion means 25.

As illustrated in FIG. 1, the directions of arrow symbols U, D, L and R are defined as operating directions of the operation lever 8. In this case, it is assumed that the trajectory of the distal end of the operation lever 8 when the operation lever 8 is tilted in the directions of the arrow symbols U and D is a direction along the insertion axis Ax of the insertion portion 2. Similarly, it is assumed that the trajectory of the distal end of the operation lever 8 when the operation lever 8 is tilted in the directions of the arrow symbols L and R is a direction that is parallel to a direction that is substantially orthogonal to the insertion axis Ax of the insertion portion 2.

Further, directions indicated by arrow symbols Ua, Da, La and Ra are defined as observation field of view directions around the insertion axis Ax as a central axis when the distal end side is viewed from the proximal end side of the endoscope 1. In this case, the arrow symbol Ua direction is the upward direction, and indicates an observation field of view in the upward direction. Likewise, the arrow symbol Da direction is the downward direction, and indicates an observation field of view in the downward direction. The arrow symbol Ra direction is the rightward direction, and indicates an observation field of view in the rightward direction.

Note that the aforementioned observation field of view directions (Ua, Da, La, Ra) are defined so as to match the up-and-down and left-and-right directions on the screen with respect to an endoscopic image that is displayed on the display screen of the display apparatus 7.

Further, as will be described in detail later, a configuration is adopted so that at the time the relation between the operating directions (U, D, L, R) of the operation lever 8 and the observation field of view directions (Ua, Da, La, Ra) obtained by the field of view switching mechanism (to be described in detail later) is, for example, a relation whereby when the operation lever 8 is operated in the arrow symbol U direction, the observation field of view direction of the endoscope 1 switches to the arrow symbol Ua direction. Similarly, a configuration is adopted so that when the operation lever 8 is operated in the arrow symbol D direction, the observation field of view direction of the endoscope 1 switches to the arrow symbol Da direction. Further, a configuration is adopted so that when the operation lever 8 is operated in the arrow symbol L direction, the observation field of view direction of the endoscope 1 switches to the arrow symbol La direction. Likewise, a configuration is adopted so that when the operation lever 8 is operated in the arrow symbol R direction, the observation field of view direction of the endoscope 1 switches to the arrow symbol Ra direction.

Note that a configuration is adopted so that, in a case where the operation lever 8 has been operated to an intermediate position between the respective arrow symbols (U, D, L, R), the observation field of view may be switched in a desired direction within a predetermined range in which switching is possible.

With respect to the remaining configuration as an endoscope system, since the configuration does not directly relate to the present invention, it is assumed that the endoscope system has approximately the same configuration as in the case of a conventional endoscope of the same type, and a description and illustration of such a configuration is omitted herein.

[Configuration of Field of View Switching Mechanism]

Next, the internal configuration of the endoscope 1 of the present embodiment, in particular, the configuration of the field of view switching mechanism, will be described in detail using FIG. 2 to FIG. 6.

As described above, respective constituent members that configure the field of view switching mechanism 10 are housed and disposed inside the distal end cover 9 (see FIG. 1) of the distal end portion of the insertion portion 2 of the endoscope 1, inside the insertion portion 2 and inside the operation portion 3.

Note that, in FIG. 2, among the constituent members inside the distal end portion of the insertion portion 2 of the endoscope 1, the schematic configuration of mainly constituent members relating to the field of view switching mechanism 10 is conceptually illustrated in a manner in which the aforementioned constituent members are taken out from the distal end portion of the insertion portion 2. Accordingly, illustration of constituent members such as a pipe member or the distal end cover 9 included in the insertion portion 2, constituent members such as the illumination unit arranged inside the distal end portion of the insertion portion 2, and the signal wire and illumination cable and the like that are inserted through the inside of the insertion portion 2 is omitted from FIG. 2.

Although to be described in detail later, as an initial simple description, the field of view switching mechanism 10 in the endoscope 1 of the present embodiment is a unit that is configured as follows. That is, the field of view switching mechanism 10 is configured so that one part (movable prism) of an optical system (optical axis bending optical system; plurality of prisms) for guiding a light beam from a subject to an image pickup optical system is configured to be freely rotatable, and when a user performs an operation that tilts the operation lever 8 of the operation portion 3 to thereby rotate one part (movable prism) of the aforementioned optical system in a predetermined direction, the direction of a light beam entering the aforementioned optical system, that is, the observation field of view direction, can be switched. A configuration is adopted so that, at the time, in response to switching of the observation field of view direction, an endoscopic image that is displayed on the display screen of the display apparatus 7 is always displayed at a normal position by causing an image pickup device 21 to rotate by a predetermined amount in a corresponding direction around the insertion axis Ax, that is, so that the up-and-down and left-and-right directions with respect to the visual observation direction of the user and the up-and-down and left-and-right directions on the display screen of the display apparatus 7 match.

Therefore, as illustrated in FIG. 2, the field of view switching mechanism 10 of the endoscope 1 of the present embodiment is mainly constituted by the operation lever 8, the operation conversion means 25, operation transmission means (22, 23, 24) and an optical axis bending optical system (11 to 18) and the like.

As described above, the operation lever 8 is operation input means that is an operation member which is provided in the operation portion 3.

The operation conversion means 25 is a constituent unit for receiving a tilting operation of the operation lever 8 and resolving the operation into a plurality of outputs. The aforementioned operation transmission means (22, 23, 24; to be described in detail later) is connected to the operation conversion means 25. A configuration is adopted so that the respective outputs into which the aforementioned tilting operation is resolved by the operation conversion means 25 are transmitted to respectively corresponding constituent portions among the operation transmission means (22, 23, 24).

The operation transmission means (22, 23, 24) is a constituent unit that receives the plurality of outputs from the operation conversion means 25, and transmits the plurality of outputs to movable portions (11, 12, 21) that will be described later. The operation transmission means (22, 23, 24) is constituted by a rotating shaft 22 as image pickup portion interlocking means and a plurality of prism rotation transmission means (23, 24).

The rotating shaft 22 is image pickup portion interlocking means that interlocks a tilting operation of the operation lever 8 with a rotational operation of the image pickup device 21 included in the image pickup portion 20.

Note that in this case the image pickup portion 20 is a constituent unit configured to include, for example, in addition to the image pickup device 21 and a driving circuit (not illustrated in the drawings) that drives the image pickup device 21 and the like, an image forming lens 19 that is an image pickup optical system which receives a light beam from a subject and causes an optical image of the subject to be formed on a light receiving surface of the image pickup device 21 and the like. The rotating shaft 22 is a rotational driving shaft member for rotating at least the image pickup device 21 among the components of the image pickup portion 20 within a plane that is parallel to the image pickup surface. Accordingly, in the present embodiment, the image pickup portion 20 that includes the image pickup device 21 is a movable portion that is rotated within a plane that is parallel to the image pickup surface by the rotating shaft 22.

In order to interlock a tilting operation of the operation lever 8 with an operation of the image pickup portion 20, the rotating shaft 22 is constituted by a rod-like rigid member that is inserted through and disposed inside the insertion portion 2 in a rotatable manner with respect to an axis that is substantially parallel to the insertion axis Ax. The proximal end side of the rotating shaft 22 is connected to the operation conversion means 25, and the distal end side of the rotating shaft 22 is connected to the image pickup portion 20. By means of the configuration, the rotating shaft 22 has a function that transmits an output from the operation conversion means 25 to the image pickup portion 20.

More specifically, the rotating shaft 22 has a function such that, based on the output results obtained by conversion by the operation conversion means 25 in accordance with a tilting operation in a predetermined direction of the operation lever 8, that is, as a result of receiving a rotational driving force in a predetermined direction, the rotating shaft 22 rotates around an axis that is substantially parallel to the insertion axis Ax (arrow symbol C3 direction in FIG. 2) and transmits the aforementioned rotational driving force to the image pickup portion 20 to cause the image pickup portion 20 to rotate around the same axis (arrow symbol C3 direction in FIG. 2) that is substantially parallel to the insertion axis Ax. Note that, in this case, although it is described here that the image pickup portion 20 rotates, it is sufficient that at least the image pickup device 21 rotates, and it is not necessary for the image forming lens 19 as the image pickup optical system that is included in the image pickup portion 20 to rotate.

The aforementioned prism rotation transmission means is configured to include two wires, namely, a first wire 23 (first transmission member) and a second wire 24 (second transmission member). Of the two wires, the first wire 23 is a pulling wire that is rotation transmission means for causing one of the movable prisms (to be described in detail later) of the aforementioned optical axis bending optical system (to be described in detail later), that is, a first prism 11 (to be described in detail later) to rotate in a predetermined direction (arrow symbol C1 direction in FIG. 2). Similarly, the second wire 24 is a pulling wire that is rotation transmission means for causing the other movable prism of the optical axis bending optical system, that is, a second prism 12 (to be described in detail later), to rotate in a predetermined direction (arrow symbol C2 direction in FIG. 2).

Note that one end of each of the first wire 23 and the second wire 24 is connected to the operation conversion means 25 and the other end of each of the first wire 23 and the second wire 24 is connected to one of the movable prisms (11, 12), respectively. According to the configuration, the aforementioned prism rotation transmission means has a function that transmits to the movable prisms (11, 12) an output obtained as a result of the operation conversion means 25 converting a received tilting operation of the operation lever 8. In this case, the first wire 23 and the second wire 24 are configured so as to be capable of rotating the movable prisms (11, 12) in a predetermined direction (C1, C2), respectively, by, for example, moving forward/rearward in a direction that is substantially parallel to an arrow symbol T direction shown in FIG. 2, that is, the insertion axis Ax. Note that a faint illustrated in FIG. 4 is an example of a more specific configuration for the purpose. The configuration illustrated in FIG. 4 will be described in detail later.

The optical axis bending optical system is constituted by a plurality of prisms (11, 12, 13) that guide a light beam from a subject to the aforementioned image forming lens 19 as an image pickup optical system, a plurality of prism supporting bases (14, 15, 16) that hold the plurality of prisms (11, 12, 13), respectively, and a plurality of support portions (17, 18) that link the respective prism supporting bases (14, 15, 16) in a freely rotatable manner.

The endoscope 1 of the present embodiment is configured to include the first prism 11, the second prism 12 and a third prism 13 as the aforementioned plurality of prisms (11, 12, 13). Among the prisms, the first prism 11 is held by a first prism supporting base 14. Further, the first prism 11 (first prism supporting base 14) is pivotally supported in a freely rotatable manner in the arrow symbol C1 direction in FIG. 2 by a first rotation support portion 17 with respect to the second prism 12 (second prism supporting base 15). Therefore, the first prism 11 is held by the first supporting base 14, and is rotatably supported by the first prism support portion 17. Further, the first prism 11 is a movable prism, and is a movable portion that is rotated in a predetermined direction by the first wire 23.

The first prism 11 has an incident surface to which an incident light beam from the subject enters, a reflecting surface that reflects the light beam that enters to the incident surface and folds (bends) the optical axis of the light beam at an angle of approximately 90 degrees, and an emission surface that emits the light beam after the light beam is reflected and the optical axis is bent by the reflecting surface. In this case, the optical axis of the light beam entering to the incident surface of the first prism 11 is taken as a first optical axis O1 as illustrated in FIG. 2 and FIG. 3. Here, the first optical axis O1 is an optical axis that defines the field of view direction. Further, the optical axis of the light beam that is reflected by the reflecting surface of the first prism 11 and is emitted from the emission surface is taken as a second optical axis O2 as illustrated in FIG. 2 and FIG. 3.

The second prism 12 is held by the second prism supporting base 15. Further, the second prism 12 (second prism supporting base 15) is pivotally supported in a freely rotatable manner in the arrow symbol C2 direction in FIG. 2 by a second rotation support portion 18 with respect to the third prism 13 (third prism supporting base 16). Therefore, the second prism 12 is held by the second supporting base 15, and is rotatably supported by the second prism support portion 18. Further, the second prism 12 is a movable prism, and is a movable portion that is rotated in a predetermined direction by the second wire 24.

The second prism 12 has an incident surface that is disposed facing the aforementioned emission surface of the first prism 11 and into which a light beam from the emission surface enters, a reflecting surface that reflects the light beam that enters into the incident surface and folds (bends) the optical axis of the light beam at an angle of approximately 90 degrees, and an emission surface that emits the light beam after the light beam is reflected and the optical axis is bent by the reflecting surface. In this case, the optical axis of the light beam entering into the incident surface of the second prism 12 matches the aforementioned second optical axis O2 as illustrated in FIG. 2 and FIG. 3. Further, the optical axis of the light beam that is reflected by the reflecting surface and emitted from the emission surface of the second prism 12 is taken as a third optical axis O3 as illustrated in FIG. 2 and FIG. 3.

The third prism 13 is held by the third prism supporting base 16. The third prism supporting base 16 is fixed to a fixing portion 26 (see FIG. 3) inside the insertion portion 2.

The third prism 13 has an incident surface that is disposed facing the aforementioned emission surface of the second prism 12 and into which a light beam from the aforementioned emission surface enters, a reflecting surface that reflects the light beam that enters from the incident surface and folds (bends) the optical axis of the light beam at an angle of approximately 90 degrees, and an emission surface that emits the light beam after the light beam is reflected and the optical axis is bent by the reflecting surface. In this case, the optical axis of the light beam entering into the incident surface of the third prism 13 matches the aforementioned third optical axis O3 as illustrated in FIG. 2 and FIG. 3. Further, the optical axis of the light beam that is reflected by the reflecting surface and emitted from the emission surface of the third prism 13 is taken as a fourth optical axis O4 as illustrated in FIG. 2 and FIG. 3. The fourth optical axis O4 is taken as being substantially orthogonal to the image pickup surface of the image pickup device 21 and located at approximately a central portion of the aforementioned image pickup surface.

Note that the aforementioned plurality of support portions (17, 18) are formed in the shape of a hollow pipe as illustrated in FIG. 3. The hollow portions are portions that are provided to allow a light beam that is transmitted through each of the aforementioned prisms (11, 12, 13) to pass through the hollow portions.

One end of the first rotation support portion 17 is fixed to the first prism supporting base 14 on the first prism 11 side, and the other end of the first rotation support portion 17 is pivotally supported in a freely rotatable manner with respect to the second prism supporting base 15 (incident surface side) on the second prism 12 side. By means of the configuration, the first rotation support portion 17 pivotally supports the first prism 11 in a freely rotatable manner with respect to the second prism 12.

One end of the second rotation support portion 18 is fixed to the third prism supporting base 16 on the third prism 13 side, and the other end of the second rotation support portion 18 is pivotally supported in a freely rotatable manner with respect to the second prism supporting base 15 (reflecting surface side) on the second prism 12 side. By means of the configuration, the second rotation support portion 18 pivotally supports the second prism 12 (integrally in a state in which the first prism 11 is mounted on the second prism 12) in a freely rotatable manner with respect to the third prism 13.

[Configuration Example of Prism Rotation Transmission Means]

An example of the configuration of the prism rotation transmission means among the members included in the operation transmission means is briefly described hereunder using FIG. 4 and FIG. 5. Note that, in FIG. 2, a form is illustrated in which the first wire 23 is connected to the first prism supporting base 14, and the second wire 24 is connected to the second prism supporting base 15, respectively. In contrast, in FIG. 4, a form is illustrated in which the first wire 23 is connected to the first rotation support portion 17, and the second wire 24 is connected to the second rotation support portion 18, respectively. Either of the configurations may be adopted since it is sufficient that the configuration is one in which the first wire 23 and the second wire 24 function as prism rotation transmission means, and the first prism 11 and the second prism 12 can be rotated in predetermined directions (C1 or C2 direction), respectively. Further, in FIG. 4, because two movable prisms and the moving mechanisms of the movable prisms are illustrated, illustration of the third prism 13 as a fixed member is omitted.

As illustrated in FIG. 4, in the field of view switching mechanism 10 in the endoscope 1 of the present embodiment, the first wire 23 as prism rotation transmission means is a pulling wire that is rotation transmission means configured to transmit a driving force for rotating the first prism 11 (first prism supporting base 14 and first rotation support portion 17) in the arrow symbol C1 direction in FIG. 4.

As described above, the first wire 23 is extended from the operation conversion means 25 (see FIG. 2 and the like) of the operation portion 3, and after passing through a fixed plate 31 that holds the first wire 23, is wound around the first rotation support portion 17 (or the first prism supporting base 14), and thereafter one end portion of the first wire 23 is fixed to the aforementioned fixed plate 31 through an urging spring 33. In this case, as illustrated in FIG. 5, the first wire 23 is fixed at a contacting portion 27 with the first rotation support portion 17 (or first prism supporting base 14). Note that, to ensure that the first wire 23 that is wound around the first rotation support portion 17 (or first prism supporting base 14) does not slip off, a concave groove-shaped pulley groove in which the first wire 23 is engagingly disposed is formed in the first rotation support portion 17 (or the first prism supporting base 14).

Note that, in order to define the pulling direction of the first wire 23, the fixed plate 31 is fixed to the second prism supporting base 15 that rotates together with the second prism 12 (second prism supporting base 15).

Further, one end of a coil tube 28 that has flexibility is fixed to the fixed plate 31. The first wire 23 is inserted through the inside of the coil tube 28 in a manner enabling forward and rearward movement of the first wire 23. The other end sides of the first wire 23 and the coil tube 28 are connected to the operation conversion means 25 that will be described later.

The reason for adopting the configuration is as follows. That is, in a case where the second prism 12 rotates, it is undesirable for the first prism 11 to be rotated unintentionally interlockingly with rotation of the second prism 12.

For example, in a case where the fixed plate 31 that holds the first wire 23 and the coil tube 28 is disposed at a separate location to the second prism 12 (second prism supporting base 15), when the second prism 12 (second prism supporting base 15) is rotated in the arrow symbol C2 direction by means of the second wire 24, a positional change will arise with respect to the positional relation between the end of the coil tube 28 and the first rotation support portion 17 (or the pulley groove of the first prism supporting base 14). Since the wire 23 will be pulled or slackened as a result, the first prism 11 will rotate (which indicates unintended behavior).

Therefore, by fixing the fixed plate 31 to the second prism supporting base 15, regardless of which way the second prism 12 (second prism supporting base 15) is rotated in the arrow symbol C2 direction by the second wire 24, the positional relation between the end of the coil tube 28 and the first rotation support portion 17 does not change, and since the wire 23 does not change position during the time, the first prism 11 does not rotate in the C1 direction.

By means of the configuration, for example, when the first wire 23 is pulled in the arrow symbol T1 direction shown in FIG. 4 and FIG. 5, the first rotation support portion 17 rotates in the arrow symbol C1 (R) direction in FIG. 4 and FIG. 5. Accordingly, the direction in which the incident surface of the first prism 11 that is mounted on the first rotation support portion 17 is facing switches to a rotational direction around the aforementioned arrow symbol C1 (around the optical axis O2).

Further, when the force amount that is pulling the first wire 23 is released, the first rotation support portion 17 rotates in the arrow symbol C1 (L) direction in FIG. 5 under the urging force of the urging spring 33 and returns to the neutral position.

Note that a similar configuration is also provided for causing the first prism 11 (first rotation support portion 17) to rotate in the arrow symbol C1 (L) direction in FIG. 4 and FIG. 5. That is, although not illustrated in the drawings, a pair of the first wire 23 and a mechanism for pulling the first wire 23 are respectively provided for right (R) direction rotation pulling and for left (L) direction rotation pulling.

On the other hand, the second wire 24 is a pulling wire as rotation transmission means configured to transmit a driving force for integrally rotating the second prism 12 (second prism supporting base 15 and second rotation support portion 18) in the arrow symbol C2 direction in FIG. 4 in a state in which the first prism 11 (first prism supporting base 14 and first rotation support portion 17) is mounted on the second prism 12 (second prism supporting base 15 and second rotation support portion 18).

Similarly to the above described first wire 23, the second wire 24 is inserted, in a manner that enables forward and rearward movement, through the inside of a coil tube 28 that has flexibility and which has one end fixed to the fixed plate 31. The other ends of the second wire 24 and the coil tube 28 are connected to the operation conversion means 25 that will be described later.

As described above, the second wire 24 and the coil tube 28 are extended from the operation conversion means 25 (see FIG. 2 and the like) of the operation portion 3, and after passing through a fixed plate 32 that holds the second wire 24, the second wire 24 is wound around the second rotation support portion 18 (or fixed to the second prism supporting base 15), and thereafter one end portion is fixed to the aforementioned fixed plate 32 through an urging spring 33. In this case, similarly to the aforementioned first wire 23, the second wire 24 is fixed at a contacting portion 27 with the second rotation support portion 18 (or second prism supporting base 15) (see FIG. 5). Note that the fixed plate 32 is fixed to a fixing portion inside the insertion portion 2.

By means of the configuration, for example, when the second wire 24 is pulled in the arrow symbol T1 direction shown in FIG. 4 and FIG. 5, the second rotation support portion 18 rotates in the arrow symbol C2 (D) direction in FIG. 4 and FIG. 5. Accordingly, the direction in which the incident surface of the first prism 11 that is integrally mounted on the second prism 12 that rotates by means of the second rotation support portion 18 is facing switches to a rotational direction around the aforementioned arrow symbol C2 (around the optical axis O3).

Further, when the force amount that is pulling the second wire 24 is released, the second rotation support portion 18 rotates in the arrow symbol C2 (U) direction in FIG. 5 under the urging force of the urging spring 33 and returns to the neutral position.

Note that a similar configuration is also provided for causing the second prism 12 (second rotation support portion 18) to rotate in the arrow symbol C2 (U) direction in FIG. 4 and FIG. 5. That is, although not illustrated in the drawings, a pair of the second wire 24 and a mechanism for pulling the second wire 24 are respectively provided for downward (D) direction rotation pulling and for upward (U) direction rotation pulling.

[Configuration Example of Operation Conversion Means]

Next, an example of an interlocking configuration with respect to the image pickup portion interlocking means among the components of the operation conversion means is briefly described hereunder using FIG. 6.

As illustrated in FIG. 6 and as described above, in the field of view switching mechanism 10 of the endoscope 1 of the present embodiment, the operation lever 8 as operation input means is interlocked with the rotating shaft 22 as image pickup portion interlocking means through the operation conversion means 25.

That is, a tilting operation of the operation lever 8 is resolved by the operation conversion means 25 and outputted to the prism rotation transmission means (23, 24), and simultaneously outputted to the image pickup portion interlocking means (rotating shaft 22). By this means, when the operation lever 8 is tilted in a predetermined direction, the first prism 11 and second prism 12 are rotated in a predetermined direction by the prism rotation transmission means (23, 24), and at the same time, the image pickup portion interlocking means (rotating shaft 22) causes the image pickup portion 20 to rotate around the optical axis O4 within a plane that is parallel to the image pickup surface. The operation means that the display direction of an endoscopic image that is displayed on the display screen of the display apparatus 7 is switched.

In this case, the principal components of the operation conversion means 25 which is configured to interlock the operation lever 8 and the image pickup portion interlocking means (rotating shaft 22) are, in general, configured as follows.

That is, in order to interlock a tilting operation of the operation lever 8 with the image pickup portion interlocking means (rotating shaft 22), an interlocking cam member 35 as one part of the constituent portions in the operation conversion means 25 is interposed between the operation lever 8 and the image pickup portion interlocking means (rotating shaft 22). The interlocking cam member 35 is provided within the operation conversion means 25 provided inside the operation portion 3, and as illustrated in FIG. 6, the proximal end side of the rotating shaft 22 is fixed to the interlocking cam member 35 so as to be coaxial with the axis Ax1. A bottomed cam groove 35a with which one end 8a of the operation lever 8 engages is formed in an outer circumferential face of the interlocking cam member 35. The cam groove 35a, for example, is formed to have a cam strip that is inclined at an angle of approximately 45 degrees with respect to the axis Ax1 that is the center of rotation of the rotating shaft 22. By means of the configuration, the cam groove 35a functions as operation conversion means configured to receive tilting operations (for example, in the directions of arrow symbols U, D, L, R) of the operation lever 8 and rotate the rotating shaft 22 in the arrow symbol C3 direction.

That is, when the operation lever 8 is tilted in a predetermined direction by the user, the one end 8a of the operation lever 8 moves along the cam groove 35a in accordance with the tilting operation. As a result, the interlocking cam member 35 rotates around the axis Ax1. As described above, since the proximal end side of the rotating shaft 22 is coaxially fixed to the interlocking cam member 35, when the interlocking cam member 35 rotates around the axis Ax1 (in the direction of the arrow symbol C3 in FIG. 6), the rotating shaft 22 also rotates in the same direction. Further, as described above, because the image pickup portion 20 is fixedly installed on the distal end side of the rotating shaft 22, when the rotating shaft 22 rotates in the arrow symbol C3 direction, the image pickup portion 20 rotates around the optical axis O4 (see FIG. 2 and the like) that is coaxial with the axis Ax1 within a plane that is parallel with the image pickup surface.

Note that the interlocking mechanism with respect to the prism rotation transmission means (23, 24) that is realized by the operation conversion means 25 resolves an operation of the operation lever 8 into two axial directions that are orthogonal to each other, and converts each of the operations to a positional change in the respective wires and transmits the respective positional changes. The details of the configuration are described in detail above in the description relating to FIG. 4 and FIG. 5 (refer to the "[Configuration example of prism rotation transmission means]" section).

The operation conversion means configured as described above is configured so that the sum of the rotation angles of the first prism 11 and the second prism 12, and the rotation angle of the image pickup portion 20 become equal. Thus, the operation conversion means 25 is configured so that an image acquired by the image pickup surface of the image pickup device 21, that is, the image pickup portion 20, does not rotate on the display screen when the operation conversion means rotates the two prisms (first prism 11 and second prism 12), respectively. In this case, rotation of each prism (first prism 11 and second prism 12) in both the forward direction and reverse direction from a reference position that takes the image pickup surface (display image) as a predetermined normal position is possible. Accordingly, the rotational direction of the image pickup portion 20 is also determined in accordance with the rotational direction of each prism (first prism 11 and second prism 12). However, the display image can be subjected to inversion processing or mirror image processing by performing electrical processing on image data. Therefore, in the description of the present embodiment, the correspondence relation between the rotational direction of each prism (first prism 11 and second prism 12) and the rotational direction of the image pickup portion 20 is not expressly mentioned in particular, and it is possible to cause the aforementioned rotational directions to correspond in any way.

[Actions]

Actions when using an endoscope system including the endoscope 1 of the present embodiment configured as described above are as follows.

When using the endoscope system including the endoscope 1 of the present embodiment, as illustrated in FIG. 7, a user 100 stands facing a patient (subject) 101 lying on a bed 110, in a state in which the user 100 holds in his/her hand the operation portion 3 of the endoscope 1. At the time, the user 100 directs the distal end portion of the insertion portion 2 of the endoscope 1 to an observation site (affected part; subject) 101a in the patient 101. Thereupon, an endoscopic image acquired by the image pickup portion 20 of the endoscope 1 is displayed as illustrated in FIG. 7 on the display screen of the display apparatus 7.

In this case, the up-and-down and left-and-right directions of the endoscopic image displayed on the display screen of the display apparatus 7 match the up-and-down and left-and-right directions when the user 100 visually observes the observation site 101a. In FIG. 7, the fact is indicated by an upward arrow "↑" that is displayed within the display screen of the display apparatus 7 and an upward arrow "T" that is shown at the observation site 101a.

In this state, the user 100 can switch the observation field of view direction by tilting the operation lever 8 in a desired direction.

For example, let us assume that the operation lever 8 is tilted in the direction of the arrow symbol L or R shown in FIG. 1, FIG. 2, FIG. 6 and the like. Thereupon, the tilting operation of the operation lever 8 in the direction of the arrow symbol L or R is resolved by the operation conversion means, and the first wire 23 that is the aforementioned prism rotation transmission means is pulled by a predetermined amount, and at the same time the rotating shaft 22 that is the aforementioned image pickup portion interlocking means is rotated by a predetermined amount in a predetermined direction through the interlocking cam member 35.

In this case, the operation that pulls the first wire 23 causes the first prism 11 to rotate in the arrow symbol C1 direction shown in FIG. 2 and FIG. 4, that is, around the optical axis O2. As a result, because the direction which the incident surface of the first prism 11 faces is switched to the left-right direction, the observation field of view direction switches. In response to switching of the observation field of view direction at the time, simultaneously, by the rotating shaft 22 rotating in the arrow symbol C3 direction around the axis Ax1, the up-and-down and left-and-right directions of the endoscopic image displayed on the display screen of the display apparatus 7 are adjusted so as to always match the up-and-down and left-and-right directions with respect to the visual observation of the user 100.

Further, for example, let us assume that the operation lever 8 is tilted in the direction of the arrow symbol U or D shown in FIG. 1, FIG. 2, FIG. 6 and the like. Thereupon, the tilting operation of the operation lever 8 in the direction of the arrow symbol U or D is resolved by the operation conversion means, and the second wire 24 that is the aforementioned prism rotation transmission means is pulled by a predetermined amount, and at the same time the rotating shaft 22 that is the aforementioned image pickup portion interlocking means is rotated by a predetermined amount in a predetermined direction through the interlocking cam member 35.

In this case, the operation that pulls the second wire 24 causes the second prism 12 to rotate in the arrow symbol C2 direction shown in FIG. 2 and FIG. 4, that is, around the optical axis O3. As a result, because the direction which the incident surface of the first prism 11 faces is switched to the up-down direction, the observation field of view direction switches. In response to switching of the observation field of view direction at the time, simultaneously, by the rotating shaft 22 rotating in the arrow symbol C3 direction around the axis Ax1, the up-and-down and left-and-right directions of the endoscopic image that is displayed on the display screen of the display apparatus 7 are adjusted so as to always match the up-and-down and left-and-right directions with respect to the visual observation of the user 100.

As described above, according to the first embodiment, since a configuration is realized in which, by performing only a single operation that tilts the operation lever 8, the first prism 11 can be caused to rotate in the left-right direction, and the second prism 12 can be caused to rotate in the up-down direction together with the first prism, switching and changing of the direction in which the incident surface of the first prism 11 faces, that is, the observation field of view direction that the first optical axis O1 that defines the field of view direction faces, can be performed extremely easily within a predetermined range in the up-and-down and left-and-right directions.

Further, an operation that switches the field of view direction can be performed by performing only a single intuitive operation that tilts the operation lever 8, and thus extremely favorable operability can be obtained.

Further, in a case where switching and changing of the observation field of view direction is performed, by causing the image pickup portion 20 to rotate around the axis Ax1 that is substantially parallel to the insertion axis Ax simultaneously with rotation of the aforementioned prism by interlocking rotation of the image pickup portion 20 with a tilting operation of the operation lever 8, the up-and-down and left-and-right directions of an endoscopic image displayed on the display screen of the display apparatus 7 can be displayed so as to always match the visual observation direction of the user.

Note that, in the above described first embodiment, a configuration is adopted so that adjustment of the up-and-down and left-and-right directions of the endoscopic image that occurs when the observation field of view direction is switched in response to a tilting operation of the operation lever 8 is performed by mechanically rotating the image pickup device 21 within a plane that is parallel to the image pickup surface in accordance with the tilting operation of the operation lever 8. However, means for rotating an image acquired by the image pickup device 21 is not limited to the aforementioned example.

For example, it is also conceivable to mount a sensor configured to detect a tilting direction and angle of the operation lever 8, and to use means configured to perform electrical image processing on an image signal acquired by the image pickup device 21 in accordance with a signal from the sensor, by using a signal processing circuit formed by a video processor or the like that is included in the external apparatus 6.

Further, the same working effects as in the foregoing first embodiment can also be realized by a form that combines the mechanical image rotation exemplified in the foregoing first embodiment and electrical image rotation by the aforementioned image processing.

Second Embodiment

Figure 8:
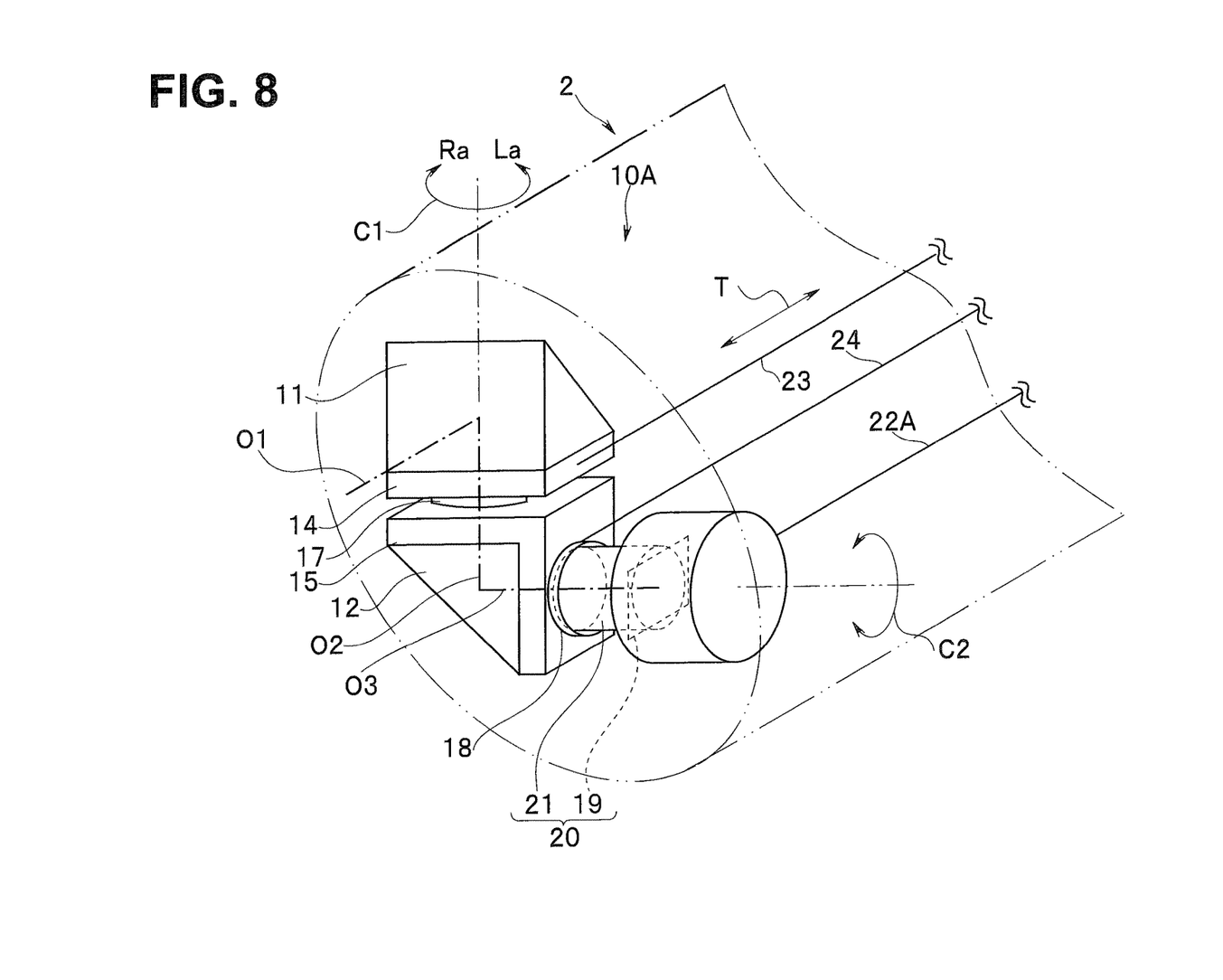
FIG. 8 is a conceptual diagram illustrating an example of the configuration of a field of view switching mechanism in an endoscope according to a second embodiment of the present invention.

Next, a second embodiment of the present invention is described hereunder mainly using FIG. 8. FIG. 8 is a view that conceptually illustrates an example of the configuration of a field of view switching mechanism in an endoscope according to a second embodiment of the present invention. The basic configuration of the present embodiment is approximately the same as in the above described first embodiment. In the present embodiment, the configuration of the field of view switching mechanism in the endoscope differs somewhat from the above described first embodiment. Therefore, components that are the same as components in the above described first embodiment are denoted by the same reference numerals as in the first embodiment and a description of such components is omitted and only a portion that is different from the first embodiment is described in detail hereunder.

FIG. 8 is a conceptual diagram illustrating one part of the field of view switching mechanism in the endoscope of the second embodiment of the present invention.

As illustrated in FIG. 8, a field of view switching mechanism 10A in the endoscope of the present embodiment is configured to include the first prism 11, the first prism supporting base 14, the first rotation support portion 17, the second prism 12, the second prism supporting base 15, the second rotation support portion 18, the first wire 23, the second wire 24 and the like.

That is, the endoscope of the present embodiment is configured without the third prism that is provided in the above described first embodiment, and the image pickup portion 20 is disposed on an extension line of the third optical axis O3. Accordingly, the image pickup device 21 of the image pickup portion 20 in the present embodiment is arranged to be freely rotatable around the third optical axis O3.

Further, consequently, in the present embodiment, the endoscope is configured without the rotating shaft 22 as the aforementioned image pickup portion interlocking means. In the present embodiment, as image pickup portion interlocking means that is used in place of the image pickup portion interlocking means in the first embodiment, for example, means is used that is configured to rotate an image on the display screen by performing electrical image processing on an image signal acquired by the image pickup device 21. Note that a component denoted by reference character 22A in FIG. 8 is an electrical signal wire that is a signal wire that is extended from the image pickup portion 20 and, for example, transmits an image pickup signal or the like that is outputted from the image pickup device 21 to the external apparatus 6. In the present embodiment, the signal wire 22A also functions as image pickup portion interlocking means.

Note that, apart from the above described configuration, naturally other configurations may also be adopted in place of or in addition to the means configured to mechanically rotate the image pickup portion 20. In this case, as means configured to mechanically rotate the image pickup portion 20, for example, a configuration is conceivable in which a drive motor or the like is disposed in the vicinity of the image pickup portion 20 to make the image pickup portion 20 freely rotatable around the third optical axis O3, and switching of the field of view is performed by rotating the first and second prisms in accordance with a tilting operation of the operation lever 8, and at the same time, driving control of the drive motor is performed to rotate the image pickup portion 20 around the third optical axis O3. The remaining configuration is the same as the configuration of the above described first embodiment.

Similar actions and effects as the actions and effects in the above described first embodiment can also be obtained by the second embodiment that is described above.

Note that the present invention is not limited to the above described embodiments, and naturally various modifications and applications can be implemented within a range that does not deviate from the gist of the present invention. Further, the above described embodiments include inventions of various stages, and various inventions can be extracted by appropriately combining a plurality of the disclosed configuration requirements. For example, if a problem to be solved by the invention can be solved and the effects of the invention are obtained even after omitting some of the configuration requirements from the entire configuration requirements described in the respective embodiments described above, then the configuration obtained by omitting the configuration requirements can be extracted as an invention. In addition, components from different embodiments may be appropriately combined. The present invention is not limited by a specific embodiment other than that the invention is limited by the accompanying claims.

INDUSTRIAL APPLICABILITY

The present invention can also be applied to endoscope apparatuses in the industrial field, and not just to endoscope apparatuses in the medical field.

What is claimed is:

1. An endoscope, comprising:
   an image pickup portion including an image pickup device;
   an optical axis bending optical system including a plurality of prisms for guiding a light beam from an object to a light receiving surface of the image pickup portion;
   an operation input member which can be pivoted;
   an operation conversion member configured to resolve an input from the operation input member and generate a plurality of outputs; and
   a plurality of operation transmission members configured to transmit the plurality of outputs that are outputted from the operation conversion member to a respectively corresponding plurality of movable portions;
   wherein:
   the operation transmission members includes an image pickup portion interlocking member that rotatably supports the image pickup portion around a longitudinal axis, and prism rotation transmission members configured to rotate the plurality of prisms of the optical axis bending optical system.

2. The endoscope according to claim 1, wherein:
   the optical axis bending optical system includes a first prism that reflects incident light from a direction of a first optical axis that defines a field of view direction, in a direction of a second optical axis that is orthogonal to the first optical axis and which is provided on a first support portion that rotatably supports the first prism around the second optical axis, and a second prism that reflects incident light from the direction of the second optical axis in a direction of a third optical axis that is orthogonal to the second optical axis and which is provided on a second support portion that rotatably supports the second prism around the third optical axis; and
   the prism rotation transmission members includes a first transmission member configured to cause the first prism to rotate around the second optical axis, and a second transmission member configured to cause the second prism to rotate around the third optical axis integrally with the first prism.

3. The endoscope according to claim 2, wherein the optical axis bending optical system further includes a third prism that reflects incident light from the direction of the third optical axis in a direction of the image pickup device.

4. The endoscope according to claim 2, wherein, in the prism rotation transmission members:
   a proximal end portion of the first transmission member is connected to the operation input member, and the first transmission member is configured to cause the first prism to rotate around the second optical axis by the first transmission member being pulled in response to a tilting operation of the operation input member, and a proximal end portion of the second transmission member is connected to the operation input member, and the second transmission member is configured to cause the second prism to rotate integrally with the first prism around the third optical axis by the second transmission member being pulled in response to a tilting operation of the operation input member.

5. The endoscope according to claim 2, further comprising:
   a first prism supporting base that holds the first prism, and to which a distal end portion of the first transmission member is connected; and
   a second prism supporting base that holds the second prism and holds the first prism supporting base in a rotatable manner around the second optical axis, and also holds the second prism integrally with the first prism supporting base in a rotatable manner around the third optical axis, and to which a distal end portion of the second transmission member is connected.

6. The endoscope according to claim 5, wherein each of the first transmission member and the second transmission member is a wire.

7. The endoscope according to claim 6, wherein:
   in the first prism supporting base, a pulley groove is formed that centers on the second optical axis, the wire is arranged in the pulley groove, and an urging spring that resists a pulling force of the wire is connected and fixed to a distal end portion of the wire; and
   in the second prism supporting base, a pulley groove is formed that centers on the third optical axis, the wire is arranged in the pulley groove, and an urging spring that resists a pulling force of the wire is connected and fixed to a distal end portion of the wire.

8. The endoscope according to claim 2, wherein:
the operation conversion member further includes an interlocking cam member comprising a cam groove that is formed at an angle of inclination of 45 degrees relative to the longitudinal axis;
the interlocking cam member is interposed between the operation input member and the image pickup portion interlocking member and interlocks the operation input member and the image pickup portion interlocking member by one end of the operation input member engaging in the cam groove and the interlocking cam member being connected to a proximal end side of the image pickup portion; and
a tilting operation of the operation input member is converted to a rotational operation around a longitudinal axis of the image pickup portion.

9. The endoscope according to claim 2, wherein the operation conversion member generates the plurality of outputs so that a sum of a rotation angle of the first prism that is caused by the first transmission member and a rotation angle of the second prism that is caused by the second transmission member, and a rotation angle of the image pickup portion that is caused by the image pickup portion interlocking member become equal.

* * * * *